United States Patent
Banister et al.

(10) Patent No.: US 8,075,856 B2
(45) Date of Patent: Dec. 13, 2011

(54) MULTIPLE REACTOR CHEMICAL PRODUCTION SYSTEM

(76) Inventors: James Andrew Banister, Poole (GB); Anthony Matthew Johnston, Double Bay NSW (AU); Brian S. Haynes, New South Wales (AU)

( * ) Notice: Subject to any disclaimer, the term of this patent is extended or adjusted under 35 U.S.C. 154(b) by 595 days.

(21) Appl. No.: 12/067,608

(22) PCT Filed: Sep. 22, 2006

(86) PCT No.: PCT/IB2006/003279
§ 371 (c)(1),
(2), (4) Date: Aug. 6, 2008

(87) PCT Pub. No.: WO2007/096699
PCT Pub. Date: Aug. 30, 2007

(65) Prior Publication Data
US 2009/0221722 A1    Sep. 3, 2009

Related U.S. Application Data

(60) Provisional application No. 60/720,330, filed on Sep. 23, 2005.

(51) Int. Cl.
*B01J 8/04* (2006.01)
*C07C 29/151* (2006.01)

(52) U.S. Cl. ........ 422/618; 422/630; 422/638; 422/642; 422/644; 422/198; 518/706; 518/712

(58) Field of Classification Search .................. 422/618, 422/630, 638, 642, 644, 198; 518/706, 712
See application file for complete search history.

(56) References Cited

U.S. PATENT DOCUMENTS

| | | | | |
|---|---|---|---|---|
| 1,603,851 A * | 10/1926 | Lummus | .......................... | 203/14 |
| 2,129,300 A * | 9/1938 | Bichowsky | .................... | 165/163 |
| 2,632,016 A * | 3/1953 | Horne et al. | .................. | 518/706 |
| 3,047,271 A * | 7/1962 | Burtt et al. | .................... | 165/166 |
| 4,665,975 A * | 5/1987 | Johnston | ....................... | 165/167 |
| 5,177,114 A | 1/1993 | Van Dijk et al. | | |
| 5,245,110 A | 9/1993 | Van Dijk | | |
| 5,383,518 A * | 1/1995 | Banks et al. | .................. | 165/166 |
| 5,424,335 A | 6/1995 | Abbott | | |
| 5,472,986 A | 12/1995 | Van Dijk | | |
| 5,765,631 A * | 6/1998 | Gerard | ........................... | 165/166 |
| 6,255,357 B1 | 7/2001 | Abbott | | |
| 6,258,860 B1 | 7/2001 | Weedon et al. | | |
| 6,723,886 B2 | 4/2004 | Allison et al. | | |
| 7,019,039 B1 | 3/2006 | Fraley | | |

FOREIGN PATENT DOCUMENTS

| | | | |
|---|---|---|---|
| EP | 483919 A2 * | 5/1992 | |
| WO | WO 98/56744 A | 12/1998 | |
| WO | WO 2007/011687 | 1/2007 | |

* cited by examiner

*Primary Examiner* — Jennifer A Leung
(74) *Attorney, Agent, or Firm* — Boyle Frederickson S.C.

(57) ABSTRACT

The present invention is a multiple reaction set for the production of chemicals by equilibrium limited reactions utilizing plate-type or extended surface heat exchangers. The heat exchangers effectively cool the reaction products in order to condense the methanol contained within the reaction products for separation, and also to warm incoming feed reactants prior to entrance of the reactants into a reactor utilized for the production of methanol. The various reactors, heat exchangers, and separators can be formed as separated zones within the enclosed vessels, thereby eliminating the need for separately constructed reactors, heat exchangers, and separators. Multi-stream plate-type of extended surface heat exchangers can be utilized to allow efficient cooling and methanol separation. The multiple reaction set can also be used for the recovery of methanol from a waste or purge gas stream utilizing multiple reactors, multiple plate-type or extended surface heat exchangers and multiple separators as a substitute for or in conjunction with a conventional methanol synthesis loop.

18 Claims, 4 Drawing Sheets

MULTIPLE REACTOR CHEMICAL PRODUCTION SYSTEM

CROSS-REFERENCE TO RELATED APPLICATIONS

This application claims priority from U.S. Provisional Patent Application Ser. No. 60/720,330, filed on Sep. 23, 2005, the entirety of which is expressly incorporated by reference herein.

BACKGROUND OF THE INVENTION

It is rare in a chemical process that the process uses stoichiometric amounts of reactants with essentially complete conversion in a simple reactor. Hence, where the reagents constitute a significant cost of the process, the unreacted material is often recycled to the reactor, usually after some physical separation of the desired product from the un-reacted material. Sometimes this separation can be achieved internally within the reactor, for example, where the reactants are gaseous, the product is in liquid form at reaction conditions and is withdrawn continuously, and a stirred tank reactor with gas induction impellers is utilized. In this particular situation, the physical separation and the recycle occurs within the reactor vessel.

Alternatively, the separation and recycle of reactant can take place external to the reactor. One example of this configuration would be a plug flow gas phase reactor where the product can be condensed from the gas phase by cooling. The unreacted gases may then be re-compressed, and at least partially returned to the inlet of the reactor, perhaps after other conditioning, such as purification or chemical separation.

There are several reasons why the amounts of reactants utilized in the reactor to form the desired end product are rarely stoichiometric. It could be that vapor pressure limitations require a non-stoichiometric reaction. For example, in high-pressure, gas-phase hydrogenations of a high boiling organic the hydrogen will be present in large excess even though a high single pass conversion of the reactant is theoretically possible. An alternate reason would be that the reaction is equilibrium limited. For example in acid catalysed esterifications the alcohol is frequently in excess to achieve high conversion of the acid.

While it may be possible to achieve high conversion of the reactants in an equilibrium limited reaction to the desired end product economically utilizing a large excess of reactants, an alternate possibility is the removal of one of the reaction products. For example, gas stripping could remove the water from an esterification reaction to continually move the conditions in the reactor out of or away from equilibrium and thereby drive the reaction toward full conversion.

However, where a product cannot be removed in-situ to drive the equilibrium toward full conversion, then a high overall conversion is likely to be achieved only by separation of the product from the reactant mixture and subsequent recycle of the un-reacted material to the reactor.

Additionally, even where an equilibrium reaction has certain conditions or aspects that are favorable for high conversion to the desired end product, the kinetics of the reaction may suggest that a higher overall production rate or better process economics can be achieved by running a reactor at conditions favoring a relatively low conversion of the reactants and then recycling the un-reacted material after physical separation of the product. Some exemplary reactions or processes of this type where conversion of the reactants to the desired product is only partial, and in which significant quantities of un-reacted material remain that can be recycled to the reactor after physical separation of the product include the reaction of synthesis gas to methanol, di-methyl ether, mixtures thereof, Fischer-Tropsch waxes, and ammonia.

Using the equilibrium limited reaction for the production of methanol as an example, because methanol is one of the largest by volume chemicals produced in the world today, the conversion to methanol is typically carried out in a two-step process. In a first step, methane is reformed with water or partially oxidized with oxygen to produce carbon monoxide and hydrogen, with some carbon dioxide and residual methane, (i.e., synthesis gas or syn-gas). In a second step, the syn-gas is converted into methanol.

The second step of converting the syn-gas into methanol is a well-known process. It typically involves a catalytic process using a copper-based catalyst, such as a catalyst comprising a reduced zinc oxide/copper oxide mixture, among others. To provide the optimum production of methanol from this reaction, the reaction is typically carried out at pressures within the range of 40-100 bars and at temperatures in excess of 200 degrees C. and below 320 degrees C., with a temperature range of between 220 and 280 degrees C. being most common. The production of the syn-gas itself is typically carried out at pressures within the range of 20-40 bars depending on the reformer technology that is utilized.

Due to the particular mechanism of the reaction for the production of methanol, the reaction does not go to completion, as the concentration of produced methanol is limited by equilibrium. Specifically, the amount of methanol contained in the product gas exiting the reactor comprises about 6-8 mol % of the total gas, although it can be higher. This methanol is removed from this product gas stream by condensing it through cooling the product gas stream to below 110 degrees C., and most commonly below 60 degrees C. The cooled methanol can then be removed from the gas stream while the excess syn-gas is sent back to the reactor in order to further react the excess syn-gas. This enables additional methanol to be obtained from the syn-gas recycled back to the reactor in combination with an amount of fresh syn-gas that is also charged to the reactor.

Figure 1:
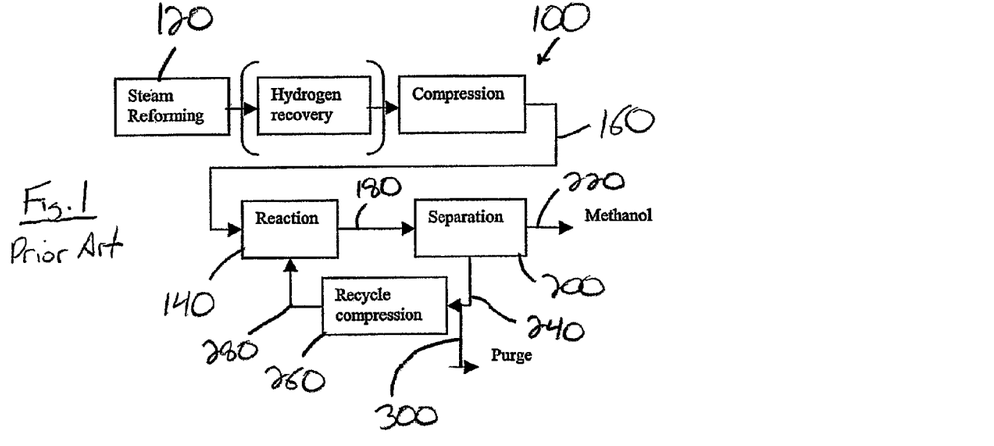
FIG. 1 is a schematic view of a prior art recycle loop reactor system.

In performing this recycle step, one well-known process involves the use of a recycle compressor which receives the excess syn-gas from the separator and compresses it in order to overcome the pressure drop that occurs within the reactor and separator. This type of reactor is commonly referred to as a recycle loop reactor and is schematically shown in FIG. 1. In this reactor, the concentration of methanol in the syn-gas leaving the reactor is low enough that the volumetric flow rate of the excess syn-gas through the recycle compressor is typically two (2) to ten (10) times the volumetric flow rate of the fresh syn-gas being introduced into the reactor separately from the syn-gas charged to the reactor from the recycle compressor. A purge gas stream of approximately 4 to 8 percent of the recycled syn-gas stream is also expelled from the recycle loop, prior to re-compression to control the concentration of inert material that builds up in the reactor as a result of the recycle.

One significant drawback to the recycle loop reactor described above is the cost of the recycle compressor. Often the recycle function is incorporated into a single drive train compressor that compresses the syn-gas up to the pressure of the recycle loop and also provides for re-compression of the recycle gases. The compression train is an expensive item of equipment and may be the single most expensive purchased component in the construction of a methanol producing facility. As stated previously, a high recycle flow is utilized to enable high overall conversion of syn-gas to be achieved. The recycle compressor also becomes significantly cheaper per unit volume compressed as the scale of the plant is increased. Thus, the use of a process using a recycle compressor is, as a practical matter, preferential for those facilities producing a relatively high daily output of methanol relative to the current maximum single train production plant, such as those facilities producing in the neighborhood of 5,000 tons per day in 2005, where maximum efficiency is required and integration of the syn-gas compressor and recycle compressor can be achieved in order to make the use of a recycle compressor economically viable.

As an alternative to a recycle loop reactor, it has been conceived that the facility could utilize a multiple reactor set or cascade process (FIG. 2) whereby the syn-gas is initially fed to a first reactor for reaction with the catalyst contained therein to produce methanol. The product gas then enters a first separator or knock-out pot wherein the methanol produced in the first reactor is cooled into liquid form and separated from the excess syn-gas. The first separator can operate to separate the methanol for the syn-gas in any desired manner, such as by gravity or by applying centrifugal focus to the products. The remaining excess syn-gas is then fed to a second reactor, which undergoes the same reaction, thereby producing additional methanol. The additional methanol is removed from the second reactor and directed to a second separator in the same manner. The number of reactors and separators can be selected to create a multiple reactor set that achieves the desired conversion percentage of the syn-gas to methanol. For example, when using an optimal syn-gas composition that has a conversion to methanol of 50 percent in each reactor, the reactor set can be selected to include four reactors and four separators, which theoretically results in the achievement of a 95 percent overall conversion of the syn-gas to methanol after the fourth separator.

However, in more realistic situations, when the syn-gas composition is less optimal, such as when the stoichiometry of the syn-gas is away from the stoichiometry of the reaction desired, e.g., the ratio ([moles hydrogen]-[moles carbon dioxide])/([moles carbon monoxide]+[moles carbon dioxide]) is between 2.5 and 3.0, then more than four reactor sets and perhaps as many as 10 reactor sets are required for high conversion (>95%). Additionally, when there are stoichiometric quantities of reactant in the syn-gas, but high levels of inerts also present, then a high number of reactor sets will be required, such as where autothermal reforming with air is performed for the production of syn-gas resulting in dilution of the syn-gas with high levels of nitrogen.

There are several areas in a methanol production process where the ability to employ a cascade of reactors would be considered beneficial. Principally the benefit from using the cascade comes from not requiring a recycle compressor. Furthermore, it should be borne in mind that in a grass roots methanol production plant the recycle compressor is often part of the compressor associated with syn-gas compression. Thus, eliminating the syn-gas compressor along with the recycle compressor in a grass roots installation gives the maximum benefit.

While the use of a simple cascade of reactors for this particular purpose is disclosed in certain prior art references, the references that discuss the use of such a cascade of reactors focus exclusively on methods by which the reformer operating pressure can be matched to the methanol synthesis pressure. For example, U.S. Pat. Nos. 5,177,114; 5,245,110; 5,472,986; and 7,019,039 are each patents that disclose inventions in the field of autothermal reforming using air rather than oxygen. However, while these patents very generally disclose the use of cascade reactors in the methanol production process, they do not address the issues of how the cascade of reactors can be made cost effectively. Furthermore, each of U.S. Pat. Nos. 5,177,114; 5,245,110; and 5,472,986 disclose a methanol production process where the recycle compressor can be eliminated as a result of operating a reformer autothermally, and then converting the syn-gas to a methoxy compound using three to five reactor sets with product condensation between each stage. Recognizing conventional wisdom that a cascade process cannot achieve a high syn-gas to methanol conversion, carbon efficiencies for the methanol synthesis section of less than 80% are quoted, whereas in conventional plant efficiencies in excess of 95% are achievable.

Additionally, U.S. Pat. No. 6,255,357 discloses a methanol production process that uses pressurization of the oxidant gas for fired heating of the steam reformer as a means of achieving an mechanically feasible high pressure steam reformer with an operating pressure sufficient to ensure a sufficient operating pressure throughout the process. The process also includes a cascade of reactors downstream from the reformer in which the reformed syn-gas is converted to methanol. The pressurization of the incoming natural gas into the reformer avoids the requirement of a syn-gas compressor upstream of the cascade of reactors, as well as avoiding the need for a recycle compressor. However, as with the previous references, the cascade of reactors is only very generally disclosed without any discussion as to how the cascade can be made economically.

Other situations regarding a methanol production process where it would be considered advantageous to avoid use of a recycle compressor include those where the compressor would be added to an existing methanol production facility in a retro-fit capacity, or as part of an addition to a planned methanol production facility construction for the purpose of removing any remaining methanol from the purge gas discharged from the facility. One system of this type that addresses the loss of the potential and actual methanol present in the purge gas stream is disclosed in U.S. Pat. No. 6,258,860, which is incorporated by reference herein in its entirety. The process disclosed directs the purge gas stream produced by a methanol synthesis zone to another methanol synthesis or production zone in order to both collect the methanol present in the purge gas stream as well as to further react the unreacted components of the purge gas stream to produce additional methanol.

However, the process disclosed in the '860 patent has certain drawbacks in that it utilizes a compressor to compress the combined purge gas and recycled syn-gas stream prior to further reacting the combined stream. Because, as discussed previously, the recycle compressor is the highest cost item in a methanol production system, the use of additional recycle compressors to recover methanol from a purge gas is highly undesirable, especially for systems producing a relatively low daily output of methanol relative to the current maximum single train production plant, such as those facilities producing in the neighborhood of 5,000 tons per day in 2005.

Another example where additional compressor capacity may be avoided through the use of a set of cascade reactors could occur as part of a re-vamp or de-bottle-necking of a methanol plant. If the re-vamp or de-bottlenecking entails increased syn-gas production, then the capacity of the methanol converter would be required to be increased. It may be possible to increase the effectiveness of the reactor through better packing of catalyst or dividing the catalyst into multiple beds in a single reactor. However, where the reactor already makes effective use of the catalyst, it may not be possible to economically increase the performance of the reactor. Further, another limitation on the operation of the reactor in this situation is the pressure drop of the process gas across the reactor. Increasing the re-circulation rate, increasing the catalyst volume, increasing the feed flow or reducing the purge rate will all increase the pressure drop of the process gas through the reactor. There will of course be a consequent limitation on the capacity of the re-circulation compressor as well to recompress the gas for reintroduction into the reactor.

One alternative to mitigate these issues would be to operate the methanol converter at reduced conversion conditions, but with a higher gas feed rate, thereby allowing pressure drop limitations to be avoided and then utilizing a separate cascade reactor system to convert the un-reacted gases to methanol without the requirement of an additional compressor or replacing the original reactor. This also has the advantage of being a lower risk method of increased throughput, as the original reactor performance is well known. There will of course be many other circumstances under which a cascade system can be utilized, but all of these circumstances will be reliant on a cost-effective design of cascade system.

One significant drawback with the multiple or cascade reactor set types utilized in methanol production as described in the prior art results from the end use construction of each reactor, heat exchanger(s) and separator forming the individual reactor set. Specifically, because a portion of the syn-gas is lost in each reactor set based on its conversion to methanol, often each subsequent reactor set and separator is constructed to be smaller than the immediately preceding ones to accommodate the reduction in the flow rate of incoming syn-gas. This might initially be anticipated to be highly beneficial based upon the reduction in the amount of material necessary to construct each successive reactor set. However, each reactor set requires the same functionality, connections, cooling and access for catalyst replacement, which become more difficult and/or expensive to manufacture on a progressively smaller scale. In addition, the cooling, gas-liquid separation and re-heating of the methanol-bearing stream as it passes between the various reactor sets must be effected in an energy efficient and cost effective manner. Further, all of the reactor sets and separators must be constructed to be operable at the elevated pressures (40-100 bars) that the reactions occurring for the conversion of the syn-gas to methanol require.

One example of a system that attempts to address this shortcoming is disclosed in U.S. Pat. No. 6,723,886 in a methanol production process using reactive distillation. However, while there is removal of methanol between reactor beds by condensation within the reactor, the condensation takes necessarily takes place at reaction temperature, and condensation at elevated temperature limits the conversion of methanol to approximately 60%. However, even with the significant restriction this places on methanol production, this is in accord with the current industry view that condensation at reduced temperature is not viable.

Therefore, it is desirable to develop a multiple or cascade reactor set and a process for the production of products of equilibrium limited reactions, e.g., methanol, using the multiple reactor set to obtain a high percentage conversion of feed syn-gas to methanol by condensing the methanol in the reactor effluent in an interstage feed/effluent heat exchanger. It is also desirable that the multiple reactor set be operable without the need for a gas recycle compressor and preferably without the need for the construction of multiple individual reactors, heat exchangers, and separators. In other terms, the heat exchanger design should be suitable for efficient operation and integration into the reactor sets, while also minimizing the number of necessary equipment items.

With regard to the goal of minimizing the necessary number of equipment items in a reactor set, it is easier to understand the conventional approach to solving this problem of eliminating equipment items and reducing the cost of equipment items by reference to the specific problems of a conventional methanol synthesis loop. Apart from the recycle compressor, a methanol synthesis loop contains six principle operations: 1) pre-heat of the gas; 2) reaction of the gas to form methanol; 3) removal of the heat of reaction as high grade heat; 4) cooling of the gas to methanol condensation temperatures; 5) condensation of the methanol using cooling water; and 6) vapor/liquid separation. In a typical plant there may be two integrations of these functions for the purposes of minimizing the necessary equipment items which are removal of the heat of reaction is performed by steam raising in a shell and tube reactor, and pre-heat of the gas by feed-effluent exchange. Thus, a typical synthesis loop will consist of at least six equipment items: 1) a start up heater; 2) a feed/effluent heat exchanger; 3) a reactor; 4) a high grade heat recovery unit; 5) a water cooler; and 6) a gas-liquid separator.

Steam raising directly in the reactor does eliminate the requirement for a separate high-grade heat recovery unit. However, it also requires a steam drum with the reactor and so does not reduce the number of equipment items.

With regard to the use of the feed/effluent heat exchanger, the highest energy efficiency is achieved with a high effectiveness heat exchanger that is able to maximize the cooling of the effluent stream. Increasing the amount of high grade heat recovered reduces the temperature difference in the feed/effluent exchanger. Therefore, for maximum high grade heat recovery a high effectiveness heat exchanger is required. However, shell and tube heat exchangers as used in prior art multiple reactor sets can only achieve high effectiveness through the coupling of multiple heat exchanger units, again increasing the number of equipment items required. The usefulness of high grade heat recovery is, in part dependent, on the temperature at which it is recovered. In particular, for a methanol process the high grade heat recovery from the methanol synthesis section is utilized for steam raising for the reformer. This requires that the stream from which heat is being recovered is above a minimum temperature, typically 200-250 deg C. However methanol condensation temperatures are in the region of 60-100 deg C. For efficient operation, therefore, heat exchangers are required that can operate with a hot gas temperature span of approximately 150 deg C. The heat of reaction is recovered by cooling the reactant stream by the equivalent of typically 50-100 deg C. of sensible heating. If the feed gas is introduced to the methanol reactor at a temperature below high grade heat recovery temperature this represents a loss of energy efficiency in the system and increases the low grade cooling requirement. Consequently the temperature difference in the feed-effluent exchanger will be kept to less than 50 deg C. and typically 20-30 deg C. Where high single pass conversions can be achieved in the reactor, such as with a balanced stoichiometry, high operating pressure, efficient heat removal or a low overall conversion the temperature constraints may be more relaxed. However, this often brings greater reactor complexity or lower overall efficiency.

The performance measure of a heat exchanger can be described in terms of temperature span and log mean temperature difference between stream. The value (span divided my lmtd) is referred to as NTU count and as can be seen above it would be desired for an energy efficient methanol process that the fee/effluent exchangers would operate with an NTU count above 5, and more preferably above 7.

The problem concerning the number of equipment items is also not alleviated when a recycle loop is replaced with a cascade system. With no recycle there is no requirement for a recycle compressor. However, for each contact with the catalyst there will be up to six additional equipment items, as discussed previously. One option to reduce the number of equipment items is to eliminate some of the heat exchangers. For example, instead of recovering high grade heat from the reactor gases, the gases can be used to directly heat the incoming feed gases. The feed/effluent exchanger is then smaller as a result of an increased driving temperature, but the reaction heat is then lost to the cooling water and a less efficient process is produced.

Therefore, to improve the economics and efficiency of the prior art methanol cascade systems, it is necessary to solve the following issues: 1) to minimize the number of equipment items; 2) to increase the effectiveness of the feed/effluent exchangers; and 3) to integrate multiple functions into single equipment items.

SUMMARY OF THE INVENTION

One method by which the improvement of the economics and efficiency of the cascade reactor system can be achieved, and which is an integral part of the apparatus and method of the present invention, is the use of extended surface, or plate style heat exchangers in the cascade reactor system. In particular, plate-fin (brazed or diffusion bonded) or printed circuit heat exchangers (PCHE) are able to achieve high effectiveness eliminating the requirement for multiple units for a single duty or a pre-heater to reduce the required effectiveness. The construction methods of plate style heat exchangers also allow for multiple stream heat exchangers to be combined into a single unit. For example, the reactor outlet gases can pass through a single plate style heat exchanger where, in a first section, the gas is cooled with a high temperature coolant such as pressurized water at 200-250 deg C. In a second section of the heat exchanger, the reactor gases are cooled by thermal contact with the reactor inlet stream. Finally, in a third section, the reactor gases are cooled with cooling water to condense the water.

When a series or cascade of reactors is used, as discussed previously, the appropriate design for heat recovery may differ as the reactor diminish in size. In the early reactors of the set the cost of heat recovery is more economical as the energy recovered per unit is greatest. With each successively smaller reactor and associated heat exchanger, the amount of energy that is available per unit diminishes as the rate of production of methanol in the set is smaller and the costs of heat recovery can become prohibitive. So, the present invention can utilize as the first reactor a steam raising or gas tube cooled reactor within a recycle loop, as discussed previously. The subsequent reactor sets each utilize a high efficiency heat exchanger of the aforementioned type integrating high grade heat recovery, feed effluent heat exchange and methanol condensation utilizing cooling water, whereas the final reactor set only utilizes a high efficiency heat exchanger for feed/effluent heat exchange and water cooling.

For even smaller methanol production units, it may also be possible to incorporate the heat exchange functions, i.e., the high efficiency heat exchangers, for each reactor set into a single fabricated unit. This is made possible by the use of plate style heat exchangers that are amenable to such construction. Additionally, separate from the integration of the heat exchangers into a single unit, integration of the reactors themselves and also the vapor/liquid separators into the same or separate units are also possible. At this smaller scale of production, the present invention can have all of the reactors contained within a single item of equipment, and all of the heat exchangers in a single unit, as well as all of the vapor/liquid separators. As a result, the cascade methanol process is effectively reduced to only three principle equipment items.

The integration of these units allows for several different uses of the integrated units. For example, a cascade reactor set unit of 3 or 4 reactors could be connected to the purge gas stream from a methanol synthesis loop to allow for the further reaction of the contents of the purge gas stream through the unit to form additional methanol. This would increase the overall conversion percentage of the loop without increasing the recycle rate, as only the purge gas is directed through the cascade reactor set unit. Also, the addition of the cascade reactor unit would both increase the amount of methanol that can be made from a fixed stream of methane, or, as part of a wider retro-fit to an existing production process, would boost the capacity of the methanol synthesis section without an increased gas rate through the recycle compressor.

Therefore, according to a first aspect of the present invention, an improved multiple or cascade reactor set type chemical production system is provided in which the incoming reaction gas entering the first reactor is an amount of excess reaction gas and/or a purge gas from a conventional single reactor, a cascade reactor set or a recycle loop reactor system, each of which are fed from a steam reformer or an autothermal reformer. The gas initially passes through a first high-efficiency plate-type or extended surface heat exchanger, whereby the incoming syn-gas comes into thermal contact with some or all the gaseous reaction products exiting the first reactor in order to cool the gaseous reaction products and preheat the incoming syn-gas. Some or all of the gases exiting the first reactor may be brought into thermal contact with an additional stream for the recovery of high grade heat prior to entering the feed-effluent heat exchange section. The cooling of the reaction products causes the desired product to condense into liquid form within the heat exchanger. Further cooling of the product bearing stream is then effected by thermal contact with an additional cooling utility stream that is also introduced into the aforementioned heat exchanger, such an arrangement being known as a multi-stream heat exchanger. The cooled reaction products, including the condensed liquid product, can be removed directly from the heat exchanger or can then flow into the first separator where the condensed liquid product is removed in the separator while the excess reaction gas is directed into a second reactor for additional production of the desired chemical. Prior to reaching the second reactor, the excess reaction gas passes through a second high-efficiency heat exchanger to be warmed by the gaseous reaction products exiting the second reactor, and consequently condenses the product contained in the product gases exiting the second reactor. The high-efficiency plate-type or extended surface heat exchangers condense the desired product, for example methanol, produced in each of the reaction zones in a highly economical manner, as each high-efficiency heat exchanger has a close temperature of approach with a counter-current design to minimize the amount of cooling water necessary and to maximize the amount of steam recovery. Further condensation is achieved through the introduction of an additional cooling stream to the high-efficiency heat exchanger so as to effect thermal contact with the product bearing stream and increase the amount of product condensed from the product bearing stream. Further, contrary to other references which state that the interstage removal of methanol by condensation is not practical or economical, such as K. R. Westerterp, New Methanol Processes, "Energy Efficiency in Process Technology" Ed. P. A. Pilarvachi, Elsevier Applied Science, 1993, pp. 1142-1153, 1147, the use of the high-efficiency plate type or extended surface heat exchangers to provide interstage methanol condensation operates in both a practical and economically viable manner within the apparatus and method of this invention.

According to another aspect of the present invention, the various reactor sets of the cascade system are formed as reaction zones integrated within a single reactor vessel, such that only the reactor vessel and appropriate inlet and outlet fittings on the vessel need to be constructed to withstand the temperatures and pressures necessary for the methanol production reaction. The reaction products from each reaction zone are passed through the high-efficiency heat exchangers which are also formed in a block-like configuration positioned and connected between each reaction zone in the reactor vessel, and a separator zone located in a separate separator vessel constructed similarly to the reactor vessel. The construction of the various reaction zones within the reactor vessel and the various separator zones within the separation vessel greatly reduces the cost of the materials necessary to construct the various vessels, as the pressure differentials between the respective zones in each of the reactor vessel and the separation vessel are minimal. This eliminates the need for constructing individual walls between the various zones of materials capable of withstanding the high pressure differentials between reaction pressure and atmospheric pressure that would otherwise be encountered.

According to still a further aspect of the present invention, an improved multiple or cascade reactor set type methanol production system is provided in which methanol is initially produced through the use of any suitable methanol production system, such as a conventional methanol synthesis loop with a recycle compressor. The purge gas stream from the methanol production system is subsequently directed through a cascade system of three or more reactor sets formed according to the present invention that further react the unreacted components of the purge gas stream to form additional methanol. The reactors are constructed separately, or as part of a single vessel with a separating wall designed to contain the differential pressure between the reactors and provide access between reactors to aid filling of the individual beds with catalyst. In each reactor set a single multi-stream heat exchanger is used to recover high grade heat, to effect feed/effluent heat exchange, and to achieve condensation of methanol by further cooling with a cooling medium such as water. In addition, the compact multi-stream heat exchangers are arranged in such a manner alongside the reactor set so as to minimize the amount of connections between the cascade reactor set and the synthesis loop.

According to still another aspect of the present invention, the multiple reactor set utilizing the high-efficiency plate-type or extended surface heat exchangers can be utilized as a stand-alone stationary or mobile system and/or as an add-on to an existing recycle loop reactor set or to an existing cascade reactor set to further increase the percent conversion of methanol from these pre-existing reactors, or maintain the overall conversion of the modified process while relaxing the effectiveness of the recycle process through, for example, a reduced recycle rate.

Numerous additional aspects, features, and advantages of the present invention will be made apparent from the following detailed description together with the drawing figures.

BRIEF DESCRIPTION OF THE DRAWINGS

The drawings illustrate the best mode currently contemplated of practicing the present invention.

In the drawings.

DETAILED DESCRIPTION OF THE PREFERRED EMBODIMENTS

With reference now to the drawing figures in which like reference numerals designate like parts throughout the disclosure, a methanol production system that can be utilized with or replaced by the present invention is indicated generally at 100 in FIG. 1. The system 100 shown is a conventional methanol synthesis loop, that receives a stream 160 of syn-gas from a reformer 120, converts a portion of the syn-gas to methanol in a reactor 140, and discharges a combined stream 180 of unreacted syn-gas and methanol to a condenser or separator 200. The combined stream 180 is separated in the separator 200 into a methanol stream 220 that is collected, and a recycle stream 240 that is directed from the separator 200 to a recycle compressor 260. The compressor 260 compresses the gas in the recycle stream 240 and directs the recompressed gas stream 280 back to the reactor 140. However, a portion of the recycle stream 240 entering the compressor 280 is diverted as a purge gas stream 300 prior to recompression.

Figure 2:
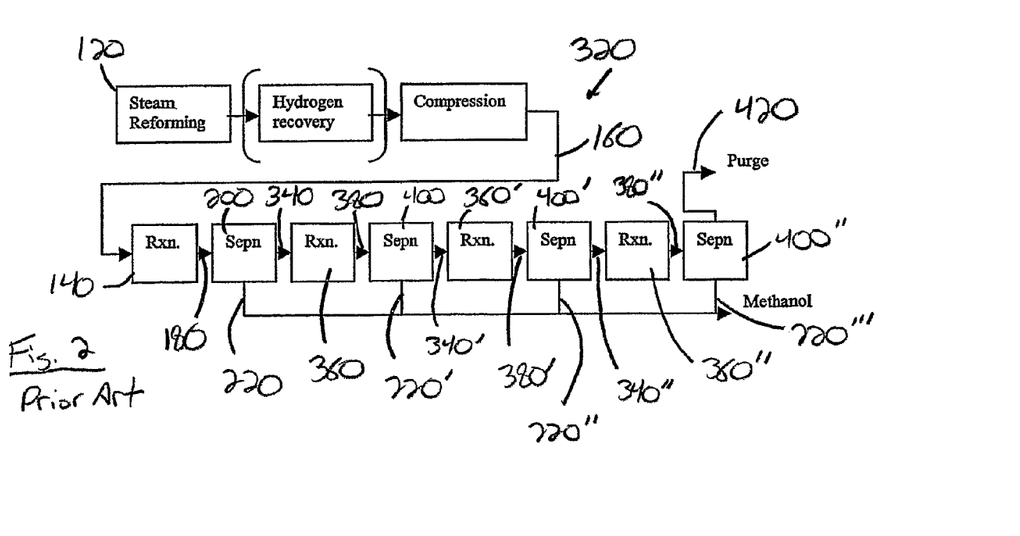
FIG. 2 is a schematic view of a prior art multiple reactor set or cascade system.

In addition, another prior art methanol production system that is capable of use with the present invention is the multiple reactor set or cascade system 320 shown in FIG. 2. Similar to the recycle system 100, the cascade system 320 also includes the reformer 120 that forms and directs a stream 160 of syn-gas to a first reactor 140 that converts a portion of the stream 160 to methanol, forming a combined stream 180 that exits the reactor 140. This combined stream 180 subsequently enters a first separator 200 where it is separated into a methanol stream 220 and a first stream 340 of excess syn-gas. This excess syn-gas stream 340 is then directed to a second reactor 360 for further reaction of the stream into methanol. The resulting second combined stream 380 is then passed to a second separator 400, where a second methanol stream 220' is formed and combined with stream 220, and a second excess syn-gas stream 340' is passed to a third reactor 360'. The third reactor 360' forms from the second excess stream 340' a third combined stream 380' that passes into a third separator 400' and which exits as a third methanol stream 220" and a third excess syn-gas stream 340". The third methanol stream 220" is combined with streams 220 and 220', and the third excess stream 340" is passed to a fourth reactor 360". The reactor 360" transforms the excess stream 340" into a fourth combined stream 380", that enters a fourth separator 400". The fourth separator 400" separates the combined stream 380" into a fourth methanol stream 220''' and a purge gas stream 420.

Figure 3:
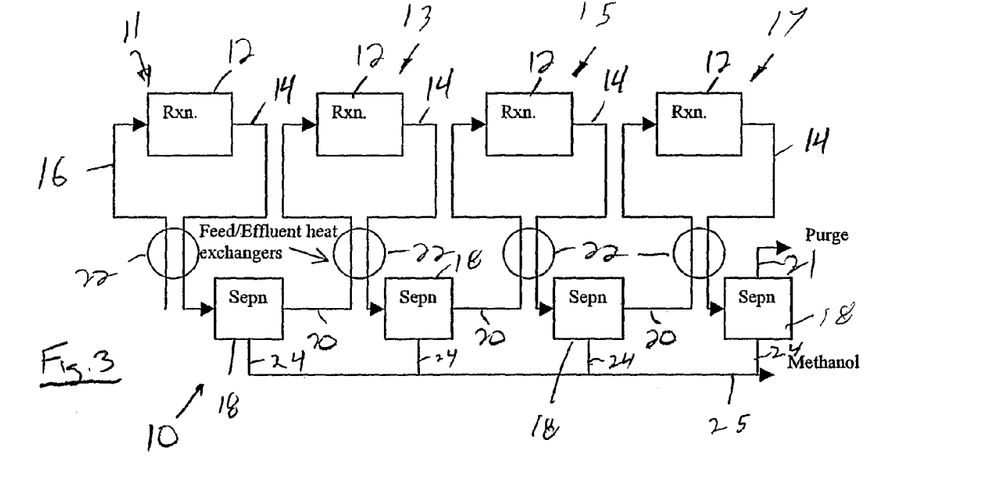
FIG. 3 is a schematic view of the multiple reactor set of FIG. 2 including a number of interstage feed/effluent heat exchangers constructed according to the present invention.

A multiple reactor set methanol production system constructed according to the present invention is indicated generally at 10 in FIG. 3. The system 10 receives a stream 16 of syn-gas from a reformer (not shown), converts the syn-gas to methanol in stages, and ultimately discharges a stream 21 of purge gas and a combined methanol stream 25. Significantly, it lacks a recycle compressor yet still operates efficiently, permitting it to be used economically in relatively small-scale applications producing less than 2,500 tons of methanol per day, and more particularly on the order of less than 1,500 or less than 1,000 tons of methanol per day. It could, however, be scaled up for larger scale operation as well or reduced in size without significant detriment.

The syn-gas typically contains approximately 66 mol % hydrogen, 20 mol % carbon monoxide, 9 mol % carbon dioxide, and 2 mol % methane. It would also contain any nitrogen that was present in the methane originally fed to the reformer where the syn-gas is made. The actual composition will depend on the pressure and temperature used in the reforming, the method of reforming (steam reforming, autothermal etc.) and whether there was any carbon dioxide added to, or present in the methane stream fed to the reformer.

The system 10 includes a number of reactor sets 11, 13, 15, 17 located in series such that each downstream reactor set receives the effluent from the immediately upstream reactor set as a feed stream, further conveys the feed stream, and discharges a condensed methanol stream 24 and an effluent stream 20. The methanol streams 24 are combined to form combined stream 25. The effluent stream from the downstream-most reactor set forms the purge gas stream 21.

Still referring to FIG. 3, each of the reactor sets 11, 13, 15, 17 includes a reactor 12, a separator 18, and a feed/effluent heat exchanger 22. Each of the reactors 12 receives a feed stream feed 16 or 20 and discharges a product stream 14. The product stream 14 from each of the reactors 12 is directed through a corresponding heat exchanger 22, where it is cooled by heat exchange from the feed stream 16 or 20 for the reactor of that set to condense the methanol from the product stream. The stream 14 is additionally cooled by the introduction of cooling utility within the structure of the feed-effluent exchanger 22 such that thermal contact is achieved. The product stream 14 of each reactor set 11, 13, 15, 17 is then directed to a corresponding separator 18 of any suitable type which, in turn, provides a return stream 20 to the reactor 12 of the next downstream reactor set. As mentioned above, the return stream 20 from the separator 18 of the final reactor set 15 is discharged as a purge gas stream 21.

The reactors 12 can be selected to be any suitable type of reactor for use in a methanol production reaction as are known in the art. Preferably each reactor consists of multiple adiabatic beds with cooling of the process fluid after each bed such that steam is produced to be used as a utility. Only two adiabatic beds per reactor are sufficient to enable the correct operation of the process. Suitable alternate reactors could be conceived by comparison with conventional methanol reactors such as steam jacketed tubes (or Lurgi reactor), a tube cooled reactor available from Davy-Synetix, an adiabatic bed reactor with more than two beds, or perhaps spherical or radial geometry multiple adiabatic bed reactors, among others. Each reactor 12 contains a methanol synthesis catalyst such as one comprising a reduced zinc oxide/copper oxide mixture. The conversion typically takes place at 40-100 bars and temperatures in excess of 200° C., typically at 220-280° C. but not exceeding 310° C. Typically the product stream 14 will contain approximately 5 mol % methanol. Higher conversion rates can be achieved at lower temperatures but at the expense of larger catalyst volumes.

The heat exchangers 22 are preferably selected to be plate-type heat exchangers, such as a diffusion bonded printed circuit heat exchanger manufactured by Heatric of Dorset, UK, or extended surface heat exchangers, such as a diffusion bonded plate fin heat exchanger available from Heatric, or a brazed plate fin heat exchanger available from Chart Industries of Bracknell, UK, a spiral wound heat exchanger, or other suitable stacked plate heat exchangers, as opposed to prior art shell and tube heat exchangers. These types of heat exchangers are preferred because plate-type or extended surface heat exchangers 22 are capable of providing a close temperature of approach to the fluid streams passing through the exchangers 22, such that the product streams exit the exchangers 22 within five (5) degrees C. of one another. This effectively minimizes the amount of cooling water required and maximizes the steam recovery from the heat exchangers 22, such that these types of heat exchangers have an effectiveness greater than 7 NTU.

The heat exchangers 22 also are capable of multi-stream and/or countercurrent operation such that multiple heat transfer operations can take place within a single heat exchanger 22. Specifically, the heat exchangers 22 effectively cool the methanol component within each of the product streams 14 to condense the methanol in the product streams 14 and enable removal of the methanol within the separators 18 in a highly economic manner. An additional cold utility stream is introduced into the heat exchanger to maximize methanol condensation. In addition, the heat retained by the product streams 14 is effectively utilized to elevate the temperature of the feed stream 16 and the return streams 20 prior to these streams 16 and 20 entering the reactors 12. Methanol typically begins to condense at 110° C., depending on concentration and reaction pressure. For efficient removal of methanol (>75%) where the exit concentration is typical (5%), then the heat exchangers 22 are preferably configured to cool the product streams 16 to below 60° C. by the incorporation of a cooling utility stream into the feed/effluent exchange reactor. Most preferably, the reactor return stream 20 can pass through a single plate style heat exchanger 22 where, in a first section, the gas is cooled with a high temperature coolant such as pressurized water at 200-250 deg C. In a second section of the heat exchanger 22, the reactor gases are then cooled by thermal contact with the reactor inlet stream 16. Finally, in a third section, the reactor gases are cooled with cooling water to condense the water.

While the system 10 shown in FIG. 3 illustrates four reactors sets 11, 13, 15, 17, the number of reactor sets and constituent components of each reactor set can be varied as desired. For instance, optimal operation of the illustrated embodiment with four reactors 12 requires a tight composition control of the syn-gas in the feed stream 16 in order to keep the stoichiometric ratio $[(H2-CO2)/(CO+CO2)]$ between 2:1 and 3:1, and preferably between 2.1-2.2/1 in order to achieve the 95 percent conversion of the syn-gas to methanol required for an economically viable process. However, by adding additional reactor sets, up to ten (10), a system would capable of producing acceptable overall syn-gas conversions (i.e., in excess of 95 percent for $CO_{(x)}$, or in excess of 90 percent for $H_2$) with a wider range of feed gas compositions having ratios between 3:1 and 2:1, and/or for feed gases with changing compositions, such as are present at CO2 stimulated gas fields.

Figure 4:
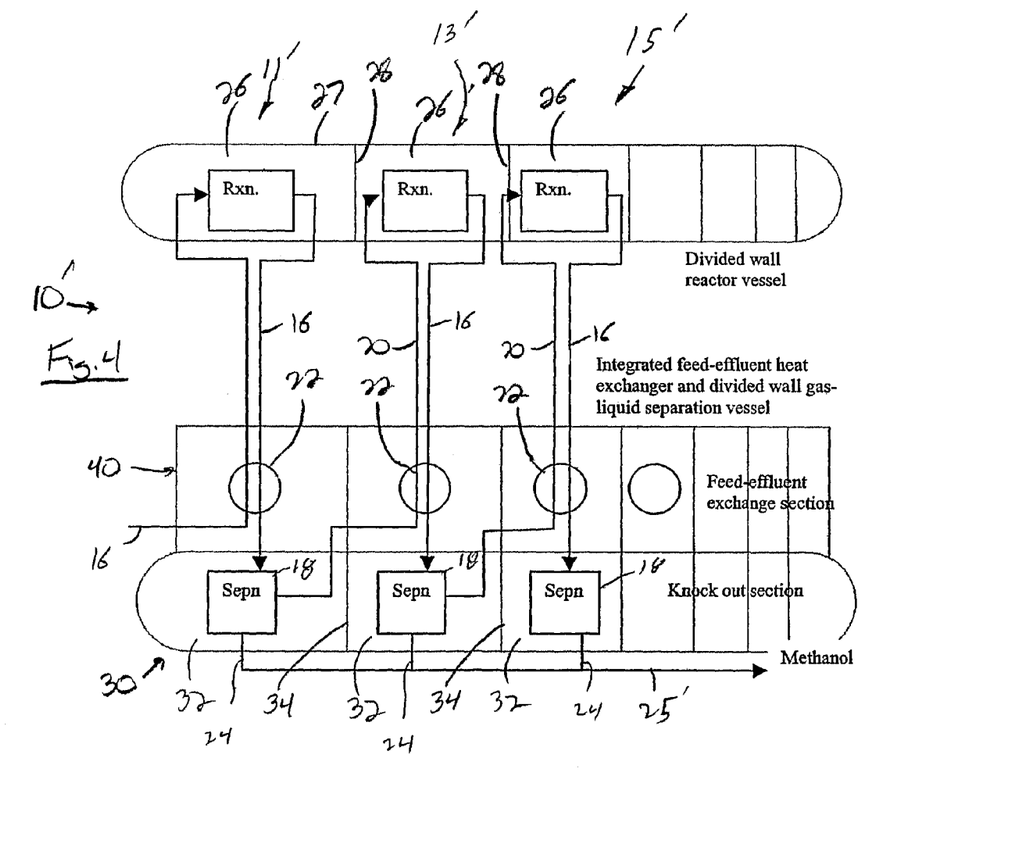
FIG. 4 is schematic view of a second embodiment of the reactor set of FIG. 3, in which the separate reactors, heat exchangers and separators are formed as zones disposed within a single vessel.

Referring now to FIG. 4, in a more specific embodiment of the invention, the system 10' includes a reactor vessel 27 that defines a number of reaction zones 26 therein, each of which contains the reactor 12 for a corresponding reactor set 11', 13', 15', etc. The system 10' also includes a separator vessel 30 which defines a number of separation zones 32 therein for each of the reactor sets 11', 13', 15', etc. The vessels 27 and 30 are constructed in a manner which allows the vessels 27 and 30 to withstand the elevated temperature (200° C. to 310° C.) and pressure (40-100 bars) required for the methanol production reaction. To separate the various reaction zones 26, dividing walls 28 are disposed between adjacent zones 26. Because all of the reaction zones 26 are disposed within the vessel 27, the only pressure differential between the zones 26 is the pressure drop between the process streams flowing into and out of successive reaction zones 26, which is typically around 0.2-2.0 bars. Thus, the dividing walls 28 are constructed of materials that only need to be able to withstand a pressure differential of around 0.2-2.0 bars, which is much less costly than the materials forming the vessel 27, and the walls 28 can be of a simple welded construction. Ease of construction may result in a design that uses more than one reactor vessel to accommodate the multiple reactor zone and more than one separation vessel to accommodate the methanol separators. Additionally, access to each of the zones 26 can be provided through the walls 28 at an internal access point (not shown) capable of withstanding 2 bars of pressure, instead of an external access point (not shown) requiring an forty (40) to one hundred (100) bar design pressure. Also, with the inclusion of the reactors 12, heat exchangers 22 and separators 18 in the various vessels 27 and 30, and heat exchanger block 40, to be discussed, the system 10 can be operated at the same pressure as the reformer (not shown) that supplies the syn-gas to the system 10, thus eliminating the need for syn-gas compression prior to being fed to the system 10.

Figure 6:
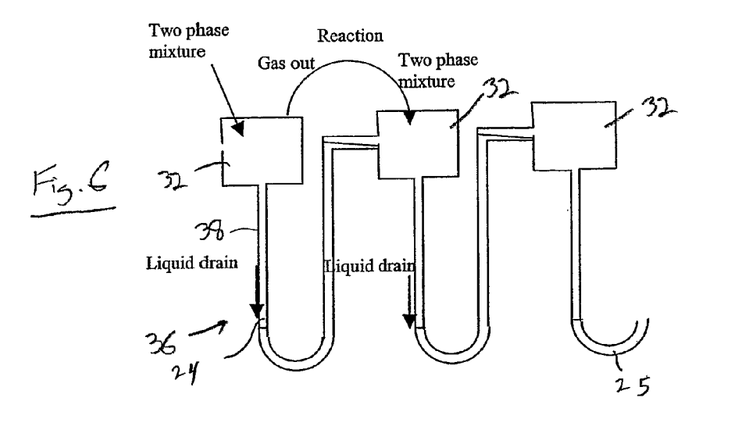
FIG. 6 is a schematic view of a weir discharge system for the separators of the reactor of FIG. 4.

Similarly, the specific embodiment of the system 10' also includes a separation vessel 30 that defines a number of separation zones 32 or knock out pots, each of which contains the heat exchanger 22 and separator 18 for a corresponding reactor set 11', 13', 15'. The separation zones 32 are separated from one another by dividing walls 34. Again, because the pressure drop between adjacent separation zones 32 is very low, e.g., less than two (2) bars, the dividing walls 34 can be constructed of materials similar to walls 28 and much less costly than the materials utilized for the construction of the separation vessel 30. Additionally, as shown in FIG. 6, due to the small pressure drop between zones 32, a weir system 36 can be utilized that connects each of the zones 32 and allows the condensed methanol stream 24 to flow from a separation zone 32 downwardly along a liquid drain 38 into an adjacent separation zone 32 under the influence of the pressure differentials between the separation zones 32. The liquid drain 38 and weir system 36 thereby allow the methanol stream 24 to flow between the respective separation zones 32 or knock-out pots to form the combined stream 25 without the need for an active level control of the methanol level within the separation zones 32 and still maintaining a gas seal. In its simplest construction, the zones 32 can be formed with a mixed phase inlet (the product stream 14), an upper gas outlet (the return stream 20), and a lower fluid outlet (the methanol stream 24) when the liquid can directly settle out of the gas in the mixed phase by gravity.

Figure 5:
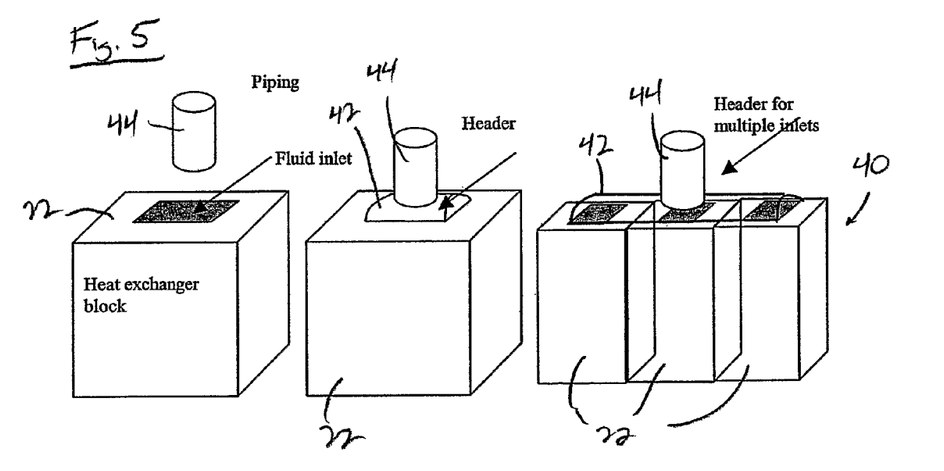
FIGS. 5A-5C are isometric views of header constructions for the feed/effluent heat exchangers of the reactor of FIG. 4.

Looking at FIGS. 4 and 5, the heat exchangers 22 can also be incorporated into a single block 40 where each of the exchangers 22 are positioned to align the entry and exit points (not shown) for the cooling fluid flowing through the exchangers 22 such that they can be connected to a header 42 that, in turn, is operably connected to piping 44 to distribute a cooling fluid flow into the inlet 45 for each of the respective heat exchangers 22. As the heat exchangers 22 are formed of extended surface or plate-type heat exchangers, such as printed circuit heat exchangers, a single header 42 can be utilized for a single fluid supplied to each of the heat exchangers 22 in order to provide the cooling water and/or heated steam to the exchangers 22. A similar type of header (not shown) but with dividing walls (not shown) can also be disposed on each exchanger 22 in the block 40 that is configured to function as a reaction zone that replaces the zones 26 in the vessel 27 by placing a reaction catalyst in the header, which receives the feed stream 14 or one of the return streams 20 from the separation zones 32. The header allows the methanol conversion reaction to take place within the header and subsequently redirects the product stream 16 with the methanol and excess syn-gas back into the heat exchanger 22 to which the header is connected.

In the particular embodiments in FIGS. 4-6 where the methanol production system 10' includes a reactor vessel 27 with multiple reaction zones 26, a block 40 with heat exchangers 22 and a separation vessel 30 with separation zones 32, the system 10' can be configured to be constructed either as a mobile unit, or a fixed unit that has the capacity to synthesize from 1 to 500 metric tons per day of methanol. Also, in addition to the use of the system 10' as a stand-alone unit, the system 10' can be connected to the purge gas stream of a recycle loop reactor or any other methanol production system to increase the conversion of the recycle loop reactor or multiple reactor set by using the purge gas as the feed stream 16 for the reactor set 10'. This use is especially advantageous where the reactor set system 10' is formed with the reactor vessel 27, heat exchanger block 40, and the separation vessel 30.

Figure 7:
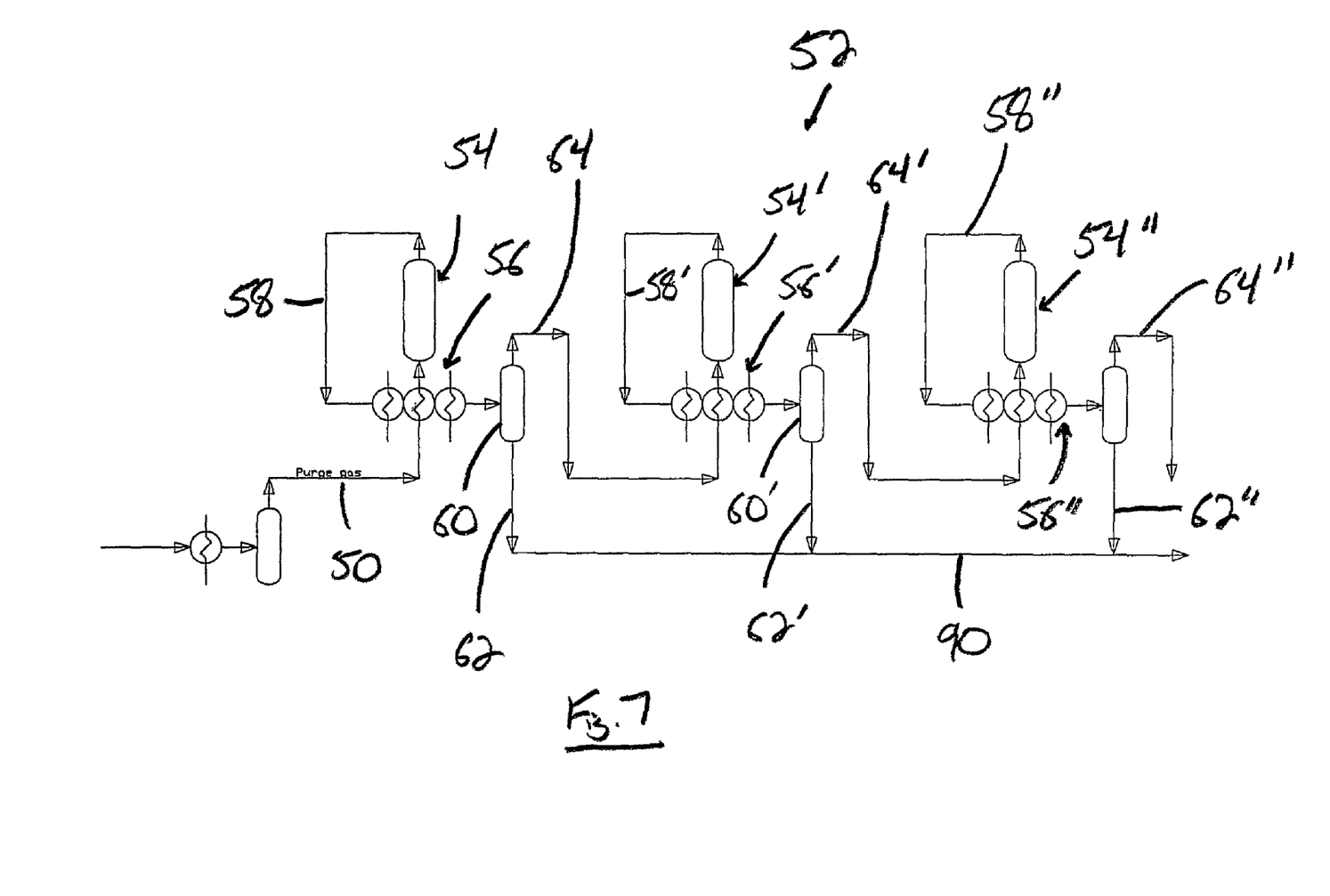
FIG. 7 is a schematic view of the reactor set of FIG. 3 attached to the purge gas stream of a methanol production reactor system.

Looking now at FIG. 7, another embodiment of the present invention is illustrated in which the system 10 is utilized as a methanol recovery system 52 that is operably connected to the purge gas stream 50 of a recycle compressor 260 of a recycle loop system 100, similarly to that described previously for the system 10'. The system 52 includes a number of reactors 54, 54', 54" operably connected to one another, and which preferably are formed as simple adiabatic reactors. The purge gas stream 50 exiting the recycle compressor 260 initially passes through the a first heat exchanger 56 to preheat the purge gas stream 50 prior to entering the first reactor 54. The purge gas stream 50 is heated by a first reactor product stream 58 that exits the first reactor 54 and passes through the first heat exchanger 56 to thermally contact and raise the temperature of the purge gas stream 50. Simultaneously, the purge gas stream 50 lowers the temperature of the first product stream 58 which consists of methanol and still unreacted purge gas. This now-cooled first product stream 58 then passes from the first heat exchanger 56 to a first separator 60 whereby the product stream 58 is further cooled to produce a first methanol stream 62 and a first unreacted purge gas stream 64. The first methanol stream 62 is collected from the first separator 60 to form a methanol product stream 90, while the first unreacted purge gas stream 64 is directed to a second heat exchanger 56' in order to cool and be heated by a second product stream 58' coming from the second reactor 54' of the methanol recovery system 52 in the same manner as described regarding first heat exchanger 56. Additionally, the second product stream 58' exiting the second reactor 54' is processed by the second heat exchanger 56' and a second separator 60' in a manner similar to the product stream 58 exiting the first reactor 54 in order to generate a second methanol stream 62' that is collected from the second separator 60' and added to the methanol product stream 90, and a second unreacted purge gas stream 64'.

The second unreacted purge gas stream 64' is directed from the second separator 60' to a third reactor 54" through a third heat exchanger 56" in the same manner as described previously regarding the passage of purge gas stream 50 and first unreacted purge gas stream 54 through heat exchangers 56 and 56'. The third reactor 54" uses the second unreacted purge gas stream 64" to generate a third product stream 58" that is directed through the heat exchanger 56" to a third separator 60" that generates a collectible third methanol stream 62" that is added to methanol production stream 90, and a third purge gas stream 54" which is discharged from the system 52.

The number of reactors 54, 54' and 54" can be varied as necessary from one to any number required for the desired methanol conversion, and can be selected to be any suitable type of reactor for use in a methanol production reaction as are known in the art. Preferably each reactor consists of a simple adiabatic reactor, and most preferably with multiple adiabatic beds, with cooling of the process fluid after each bed such that steam is produced to be used as a utility. Only two adiabatic beds per reactor are sufficient to enable the correct operation of the process. Suitable alternate reactors could be selected to be similar to those described previously as alternatives for the reactors 12 utilized in the system 10.

The heat exchangers 56, 56' and 56" are constructed similarly to the heat exchangers 22 discussed previously, and are preferably selected to be plate-type heat exchangers, such as a diffusion bonded printed circuit heat exchanger, or extended surface heat exchangers, such as a diffusion bonded plate fin heat exchanger or a brazed plate fin heat exchanger, as opposed to prior art shell and tube heat exchangers. These types of heat exchangers are preferred for the same reasons described with regard to the heat exchangers 22 utilized in the system 10, namely due to their ability to provide a close temperature of approach to the fluid streams passing through the exchangers 56, 56' and 56", and the ability of the exchangers to function in a multi-stream and/or counter current manner. This effectively minimizes the amount of cooling water required and maximizes the steam recovery from the heat exchangers 56, 56' and 56". As a result, the heat exchangers 56, 56' and 56" also effectively cool the methanol component within each of the product streams 58, 58' and 58" to condense the methanol in the product streams 58, 58' and 58" and enable removal of the methanol within the separators 60, 60' and 60" in a highly economic manner.

Further, the reactor product streams 58, 58' and 58" can be cooled by a utility stream (not shown) prior to entering the heat exchangers 56, 56' and 56". Significantly, it lacks a recycle compressor yet still operates efficiently, permitting it to be used economically in relatively small-scale applications producing on the order of 1,000 to 1,500 tons of methanol per day. It could, however, be scaled up for larger scale operation as well or reduced in size without significant detriment.

Additionally, the methanol recovery system 52 can include combination elements (not shown) which function as both each of the heat exchangers 56, 56' and 56" and separators 60, 60' and 60" to minimize the number of components utilized in the methanol recovery system 52.

Further, the methanol recovery system 52 can be utilized as a stand-alone stationary or mobile system and/or as an add-on to an existing recycle loop reactor system 100 or to an existing cascade reactor system 320 to further increase the percent conversion of methanol from these pre-existing reactors, or maintain the overall conversion of the modified process while relaxing the effectiveness of the recycle process through for example reduced recycle rate. Also, the system 52 can be used with systems 10 that produce other compounds formed via equilibrium limited reactions, such as higher alcohols or dimethyl ether, among others.

Various alternatives are contemplated as being within the scope of the following claims particularly pointing and distinctly claiming the subject matter regard as the invention.

The invention claimed is:

1. A product synthesis apparatus for the production of a product formed by an equilibrium-limited reaction, the apparatus comprising:
    a) a reactor vessel adapted to withstand the operating temperatures and pressures of the product-forming reaction, the reactor vessel including a number of reaction zones formed within the reactor vessel by dividing walls extending across the reactor vessel to define the reaction zones, the dividing walls configured to withstand the temperature and pressure differentials across each adjacent reaction zones;
    b) a separation vessel adapted to withstand the operating temperatures and pressures of the product-forming reaction, the separation vessel including a number of separation zones formed within the separation vessel by dividing walls extending across the separation vessel to define the separation zones, each dividing wall configured to withstand the temperature and pressure differentials across adjacent separation zones; and
    c) a heat exchanger block including a number of feed/effluent heat exchanger units, each unit operably connected to at least one of the reaction zones and to at least two of the separation zones.

2. The apparatus of claim 1 wherein the reactor vessel is formed as a header for the heat exchanger block.

3. The apparatus of claim 1 wherein each reaction zone includes an inlet port and an outlet port extending through the reaction vessel and each operably connected to an associated heat exchanger unit in the heat exchanger block.

4. The apparatus of claim 1 wherein each separation zone includes an inlet opening extending through the separation vessel and operably connected to an upstream heat exchanger unit, a first outlet opening extending through the separation vessel and operably connected to a downstream heat exchanger unit, and a second outlet opening extending through the separation vessel and operably connected to a product collection stream.

5. The apparatus of claim 1 wherein the heat exchanger block is integrally connected to the separation vessel.

6. The apparatus of claim 1 wherein the heat exchanger units are selected from the group consisting of brazed fin heat exchangers, printed circuit heat exchangers, diffusion bonded fin and plate heat exchangers, and spiral wound heat exchangers.

7. The apparatus of claim 1 wherein the product is selected from the group consisting of: methanol, dimethyl ether and mixtures thereof.

8. The apparatus of claim 1 wherein the feed/effluent heat exchanger units each have an efficiency of at least 5 NTU.

9. The apparatus of claim 1 wherein the feed/effluent heat exchanger units are each operably connected to a cooling utility stream used to condense the product present within the heat exchanger units.

10. The apparatus of claim 1 wherein the separation vessel includes a weir system connecting each of the separation zones and forming a product collection stream.

11. A product synthesis apparatus for the production of a product formed by an equilibrium-limited reaction, the apparatus comprising:
   a) a reactor vessel adapted to withstand the operating temperatures and pressures of the product-forming reaction;
   b) a separation vessel adapted to withstand the operating temperatures and pressures of the product-forming reaction, the separation vessel including a number of separation zones formed within the separation vessel by dividing walls extending across the separation vessel to define the separation zones, each dividing wall configured to withstand the temperature and pressure differentials across adjacent separation zones; and
   c) a heat exchanger operably connected to the reactor vessel and to at least two of the separation zones, wherein the heat exchanger comprises a feed/effluent heat exchanger unit disposed within each separation zone, each unit also operably connected to a downstream separation zone.

12. The apparatus of claim 11 wherein the feed/effluent heat exchanger units are each operably connected to a cooling utility stream and the heat exchange units are each formed with a first portion for thermally contacting a feed stream with a reaction product stream for the reactor vessel, a second portion downstream from the first portion for thermally contacting the reaction product stream with the cooling utility, and a third portion downstream from the second portion for separating the condensed product from the reaction product stream.

13. A method for the synthesis of a product formed by an equilibrium limited reaction, the method comprising the steps of:
   a) providing the apparatus of claim 1;
   b) directing a feed stream through the apparatus; and
   c) recovering a product collection stream from the apparatus.

14. The method of claim 13 wherein the feed stream is a purge gas stream from a recycle stream of a chemical production reactor utilizing a steam or autothermal reformer, and wherein the step of directing the feed stream comprises directing the purge gas stream through the apparatus.

15. The method of claim 13 wherein the feed stream is a syn-gas created in a steam or autothermal reformer.

16. The method of claim 13 wherein the step of recovering the product collection stream comprises recovering a product collection stream of less than 2,500 tons per day.

17. The method of claim 13 wherein the step of recovering the product collection stream comprises recovering a product collection stream of less than 1,500 tons per day.

18. The method of claim 13 wherein the step of recovering the product collection stream comprises recovering a product collection stream of less than 1,000 tons per day.

* * * * *